(12) United States Patent
Chen

(10) Patent No.: US 11,889,860 B2
(45) Date of Patent: Feb. 6, 2024

(54) CORE CARTRIDGE FOR ELECTRONIC CIGARETTE

(71) Applicant: Yushui Chen, Quanzhou (CN)

(72) Inventor: Yushui Chen, Quanzhou (CN)

(*) Notice: Subject to any disclaimer, the term of this patent is extended or adjusted under 35 U.S.C. 154(b) by 1136 days.

(21) Appl. No.: 16/666,102

(22) Filed: Oct. 28, 2019

(65) Prior Publication Data

US 2021/0093018 A1 Apr. 1, 2021

(30) Foreign Application Priority Data

Sep. 27, 2019 (CN) .......................... 201910927481.3
Sep. 27, 2019 (CN) .......................... 201921639707.1

(51) Int. Cl.
*A24F 40/00* (2020.01)
*A61M 11/04* (2006.01)

(52) U.S. Cl.
CPC ............ *A24F 40/00* (2020.01); *A61M 11/042* (2014.02)

(58) Field of Classification Search
CPC .......... A24F 40/00; A24F 40/10; A24F 40/40; A24F 40/42; A24F 40/48; A24F 40/485; A61M 11/041; A61M 11/042
See application file for complete search history.

(56) References Cited

U.S. PATENT DOCUMENTS

2013/0306064 A1* 11/2013 Thorens ................ A24F 47/008
128/202.21
2020/0367558 A1* 11/2020 Zhu ......................... A24F 40/42

* cited by examiner

*Primary Examiner* — Michael J Felton
*Assistant Examiner* — Daniel Edward Vakili
(74) *Attorney, Agent, or Firm* — Novoclaims Patent Services LLC; Mei Lin Wong

(57) ABSTRACT

A core cartridge for electronic cigarette includes a main housing, an atomizer, an actuator, and a leakage prevention arrangement. The main housing has a mouth piece portion, an atomizer portion, a connecting portion extended between the mouth piece portion and the atomizer portion, a liquid storage compartment formed in the connecting portion, and an air inlet. The main housing further has a vapor releasing channel extended from the atomizer portion to the connecting portion. The leakage prevention arrangement includes at least one drainage port formed in the main housing. The drainage port communicates the vapor releasing channel with the atomizer in such a manner that condensate formed on an inner surface of an outer boundary wall of the main housing is arranged to be guided to flow back to the atomizer through the drainage port.

12 Claims, 9 Drawing Sheets

CORE CARTRIDGE FOR ELECTRONIC CIGARETTE

BACKGROUND OF THE PRESENT INVENTION

Field of Invention

The present invention relates to an electronic cigarette, and more particularly to an electronic cigarette comprising a leakage prevention arrangement which is capable of preventing liquid from leaking out of a main housing.

Description of Related Arts

A conventional electronic cigarette usually comprises a supporting housing and a core cartridge accommodated in the supporting housing. The core cartridge may include an atomizer which is arranged to vaporize liquid solution. The vaporized liquid solution may then be blown out of the electronic cigarette through a vapor discharge channel when a user inhales on the electronic cigarette.

A major disadvantage of conventional electronic cigarettes such as the one described above is that when a user finishes inhaling cigarette vapor, a certain amount of condensate or residuals may be formed on an inner wall of the vapor discharge channel. When the user stops smoking the electronic cigarette, the residuals or condensate may leak through the core cartridge or the supporting housing.

As a result, there is a need to develop an electronic cigarette which has some sorts of mechanism to prevent residual or condensate from leaking out of the electronic cigarette.

SUMMARY OF THE PRESENT INVENTION

An objective of the present invention is to provide an electronic cigarette comprising a leakage prevention arrangement which is capable of preventing liquid from leaking out of a main housing.

Another objective of the present invention is to provide an electronic cigarette comprising a leakage prevention arrangement which is capable of temporarily collecting cigarette liquid residuals and condensate and allowing such residuals and condensate to be re-used for producing vapor.

An objective of the present invention is to provide a core cartridge for an electronic cigarette comprising a leakage prevention arrangement, wherein the core cartridge may be installed in a wide variety of supporting housings of electronic cigarettes.

In order to accomplish the above objective, the present invention provides a core cartridge for electronic cigarette, comprising:

a main housing having a mouth piece portion, an atomizer portion, a connecting portion extended between the mouth piece portion and the atomizer portion, a liquid storage compartment formed in the connecting portion, and an air inlet, the main housing further having an outer boundary wall and a vapor releasing channel extended from the atomizer portion to the connecting portion;

an atomizer supported in the atomizer portion of the main housing; and a leakage prevention arrangement, which comprises at least one drainage port formed in the main housing, the drainage port communicating the outer boundary wall with the atomizer in such a manner that condensate formed on an inner surface of the outer boundary wall of the main housing is arranged to be guided to flow back to the atomizer through the drainage port.

DETAILED DESCRIPTION OF THE PREFERRED EMBODIMENT

Figure 1:
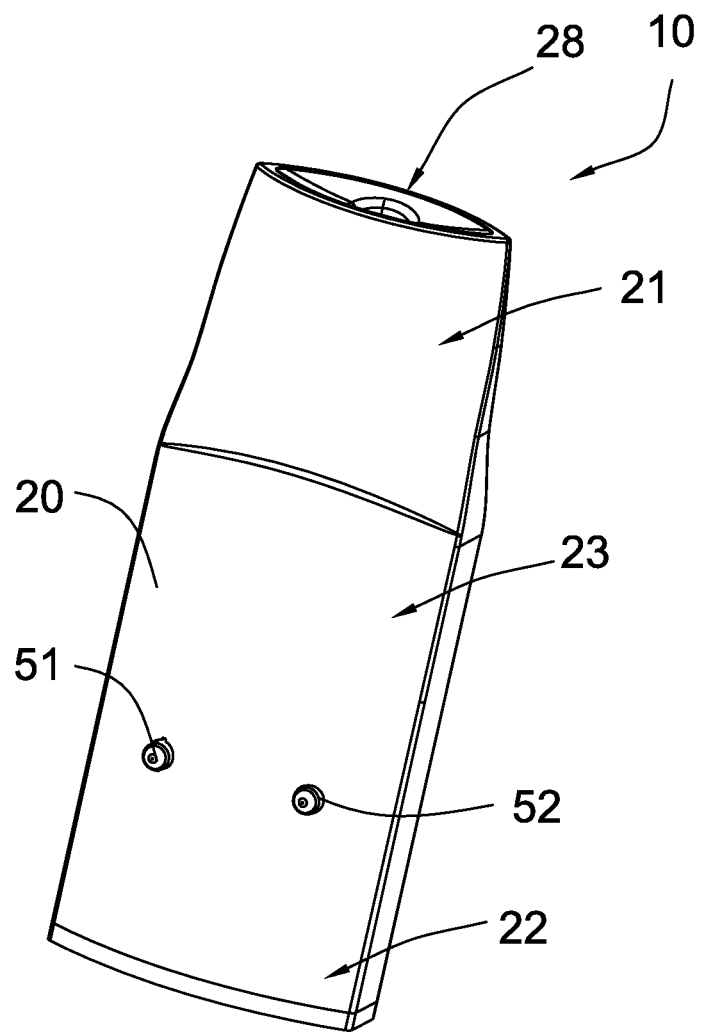
FIG. 1 is a perspective view of a core cartridge of an electronic cigarette according to a preferred embodiment of the present invention.
Figure 2:
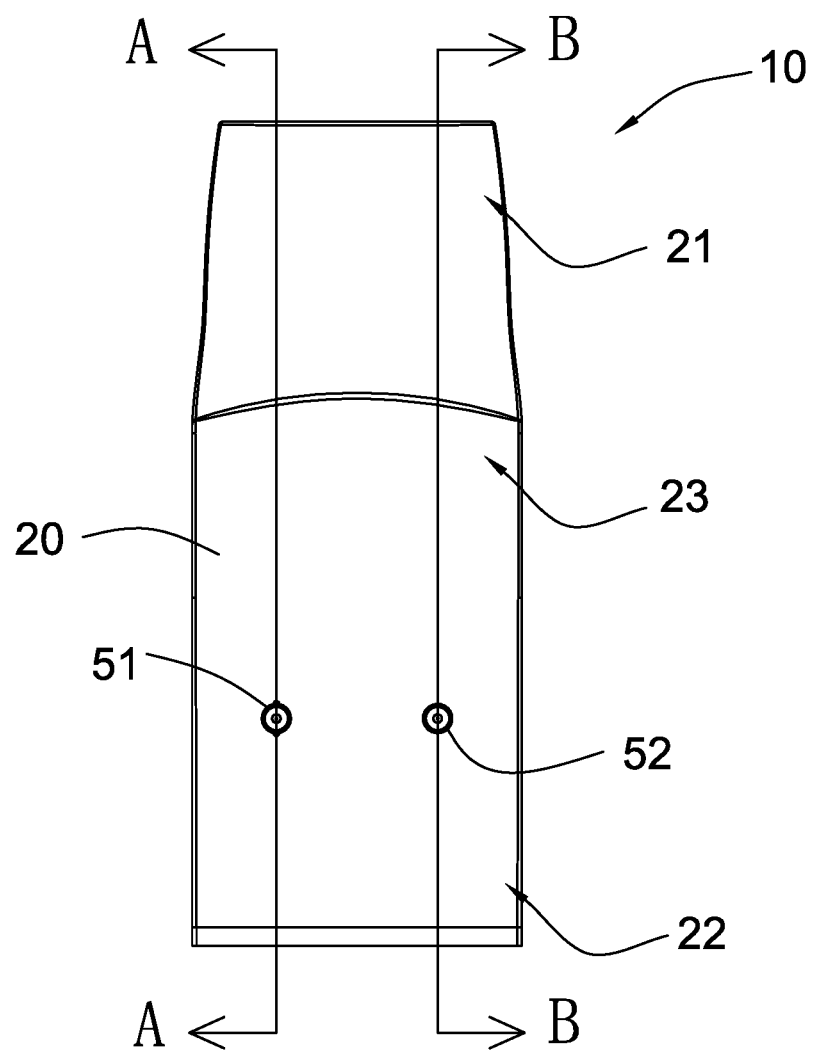
FIG. 2 is a front view of the core cartridge of an electronic cigarette according to the preferred embodiment of the present invention.
Figure 3:
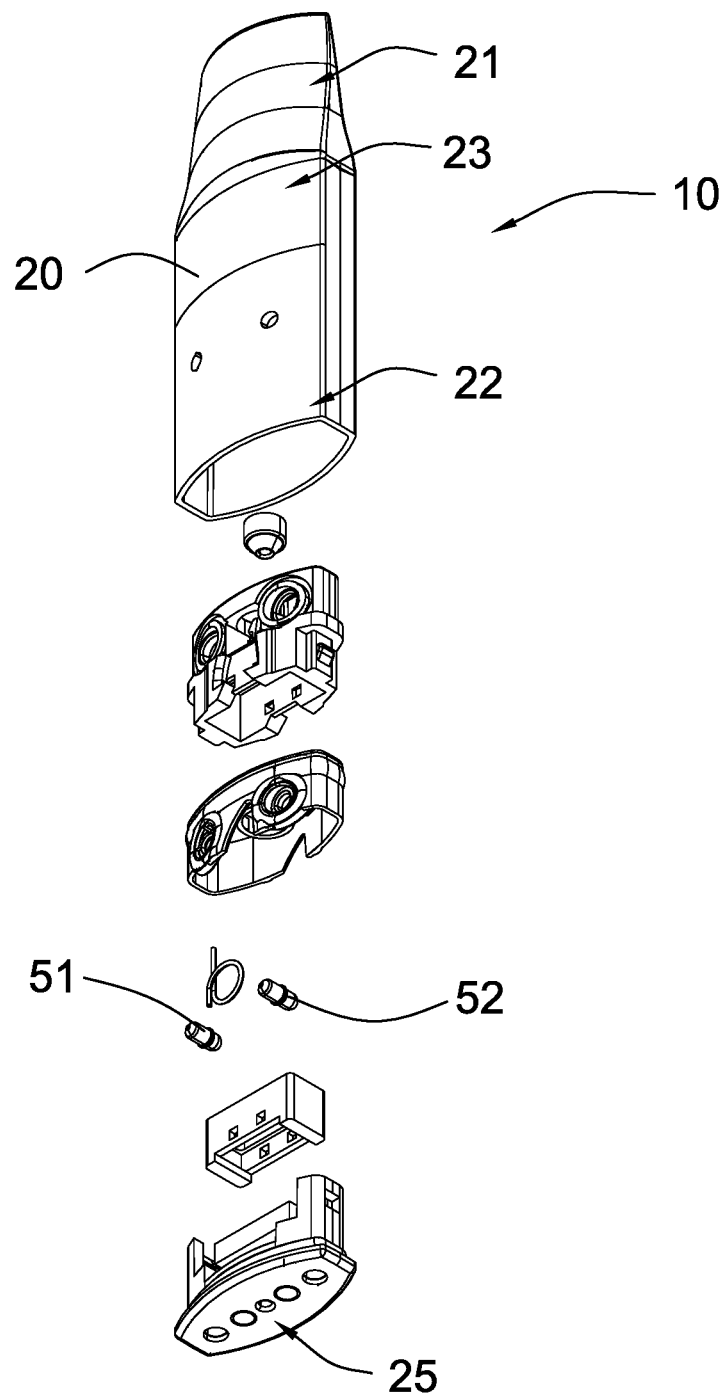
FIG. 3 an exploded perspective view of the core cartridge of the electronic cigarette according to the preferred embodiment of the present invention.

The present invention will be further described in detail in conjunction with the drawings and embodiments.

Referring to FIG. 1 to FIG. 9 of the drawings, a core cartridge 10 of an electronic cigarette according to a preferred embodiment of the present invention is illustrated. The core cartridge 10 may be supported in a housing assembly of an electronic cigarette. A user may be able to hold on the housing assembly for using the electronic cigarette. The core cartridge 10 comprises a main housing 20, an atomizer 30, and a leakage prevention arrangement 40.

The main housing 20 has a mouth piece portion 21, an atomizer portion 22, a connecting portion 23 extended between the mouth piece portion 21 and the atomizer portion 22, a liquid storage compartment 24 formed in the connecting portion 23, and an air inlet 25. The main housing 20 further has an outer boundary wall 27 and a vapor releasing channel 26 extended from the atomizer portion 22 to the connecting portion 23. The atomizer 30 may be supported in the atomizer portion 22 of the main housing 20.

The leakage prevention arrangement 40 comprises at least one drainage port 41 formed in the main housing 20. The drainage port 41 communicates the outer boundary wall 27 with the atomizer 30 in such a manner that condensate formed on an inner surface 271 of the outer boundary wall 27 of the main housing 20 may be arranged to be guided to flow back to the atomizer 30 through the drainage port 41.

According to the preferred embodiment of the present invention, the core cartridge 10 of the present invention may be fitted to a wide variety of housing assemblies of electronic cigarettes. As such, the core cartridge 10 may be actuated by the housing assemblies through different conventional actuating mechanisms. Switches 51, 52 may be provided on the main housing 20 for engaging with the corresponding housing assembly. In this preferred embodiment, the core cartridge 10 comprises an air switch 51 and a fuel switch 52 provided on the main housing 20 for switching on supply of air and fuel liquid.

The main housing 20 of the core cartridge 10 has an elongated structure when viewed from the side. The mouth piece portion 21 of the main housing 20 is ergonomically designed to fit a user's mouth. The main housing 20 further has a vapor outlet 28 formed on the mouth piece portion 21 for allowing vapor to be discharged therethrough. The vapor outlet 28 communicates with the vapor releasing channel 26 so that vapor passing through the vapor releasing channel 26 can go out of the main housing 20 through the vapor outlet 28. According to the preferred embodiment of the present invention, the mouth piece portion 21 is formed at an upper end portion of the main housing 20.

On the other hand, the atomizer portion 22 of the main housing 20 is utilized to accommodate the atomizer 30. The atomizer 30 comprises a heating element 32 for vaporizing the cigarette liquid or condensate collected by the leakage prevention arrangement 40. The heating element 32 is arranged to vaporize the e-cigarette liquid controllably released liquid storage compartment 24 when the fuel switch 52 is actuated.

The leakage prevention arrangement 40 comprises two drainage ports 41 formed in the atomizer portion 22 of the main housing 20. Each of the drainage ports 41 communicates the outer boundary wall 27 of the main housing 20 with the atomizer 30. When the electronic cigarette stops operating, residuals or condensate formed on an inner surface 271 of the outer boundary wall 27 of the main housing 20 is guided to flow through the drainage ports 41 and eventually back to the atomizer 30.

Figure 6:
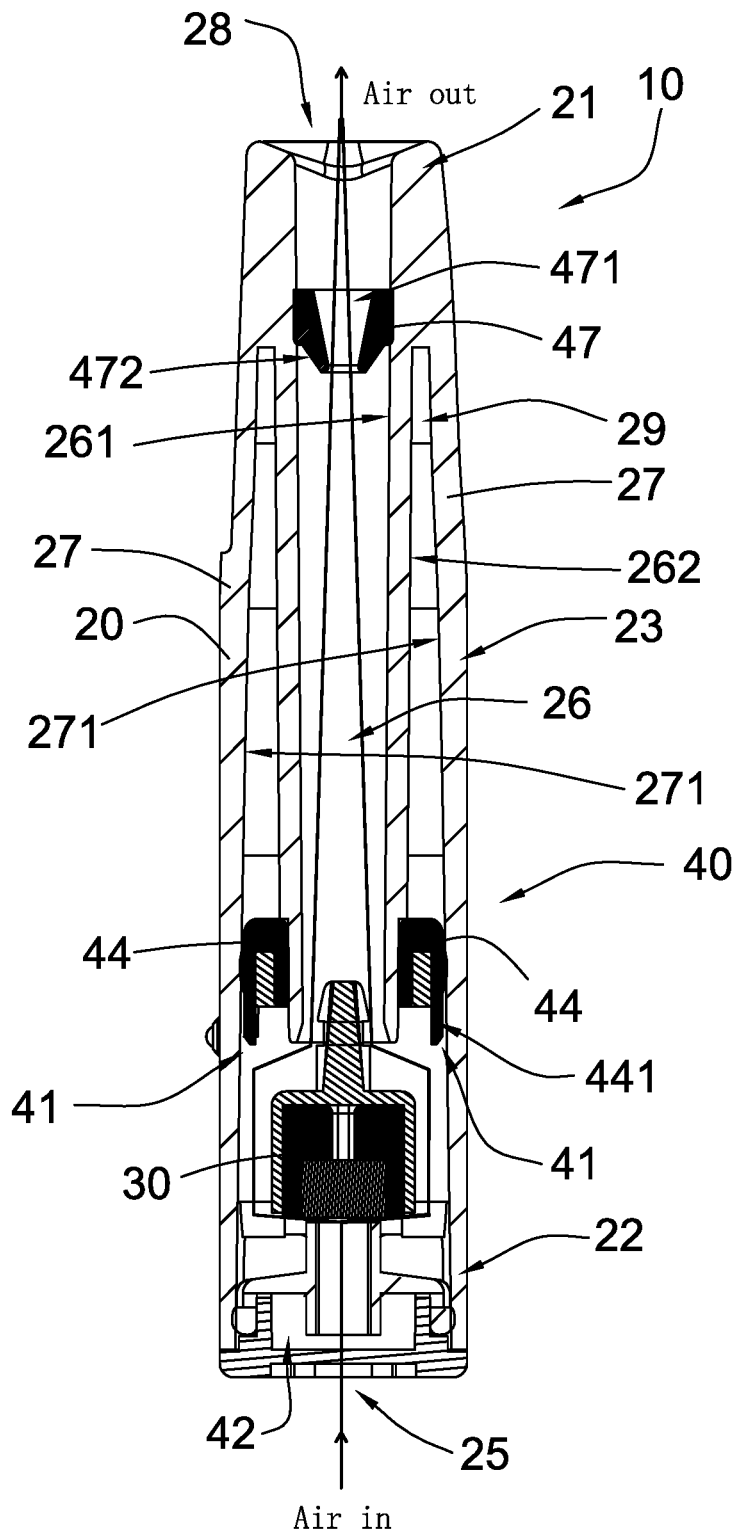
FIG. 6 is a sectional front view of the core cartridge of the electronic cigarette according to the preferred embodiment of the present invention.
Figure 7:
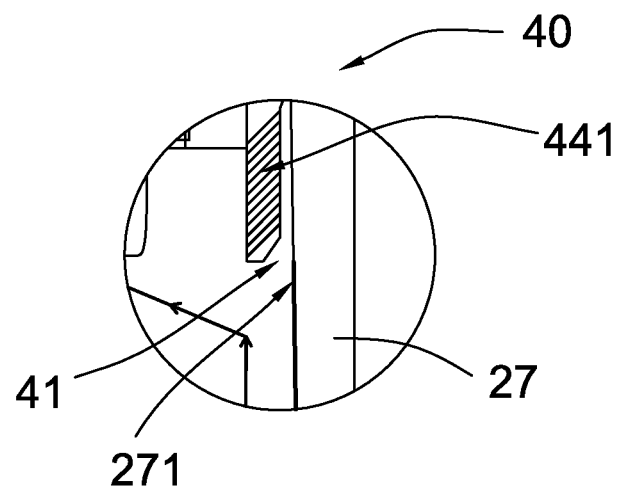
FIG. 7 is a schematic diagram of the core cartridge of the electronic cigarette according to the preferred embodiment of the present invention.

As shown in FIG. 6 and FIG. 7 of the drawings, the vapor releasing channel 26 has a tapered cross-sectional shape when viewed from the front so that the inner sidewall 261 of the vapor releasing channel 26 is inclinedly extended from the mouth piece portion 21 to the atomizer portion 22. A vapor collection cavity 29 is formed between an outer sidewall 262 of the vapor releasing channel 26 and the corresponding inner surface 271 of the outer boundary wall 27 of the main housing 20. Due to the tapered shape of the vapor releasing channel 26, the outer sidewall 262 may be slightly inclined. Likewise, the inner surface 271 of the outer boundary wall 27 can also be slightly inclined so that a thickness of the vapor collection cavity 29 is gradually increasing from the mouth piece portion 21 toward the atomizer portion 22. In this preferred embodiment, there are two vapor collection cavities 29 formed in the main housing 20, wherein the vapor collection cavities 29 are formed on a front side and a rear side of the vapor releasing channel 26 respectively.

Figure 4:
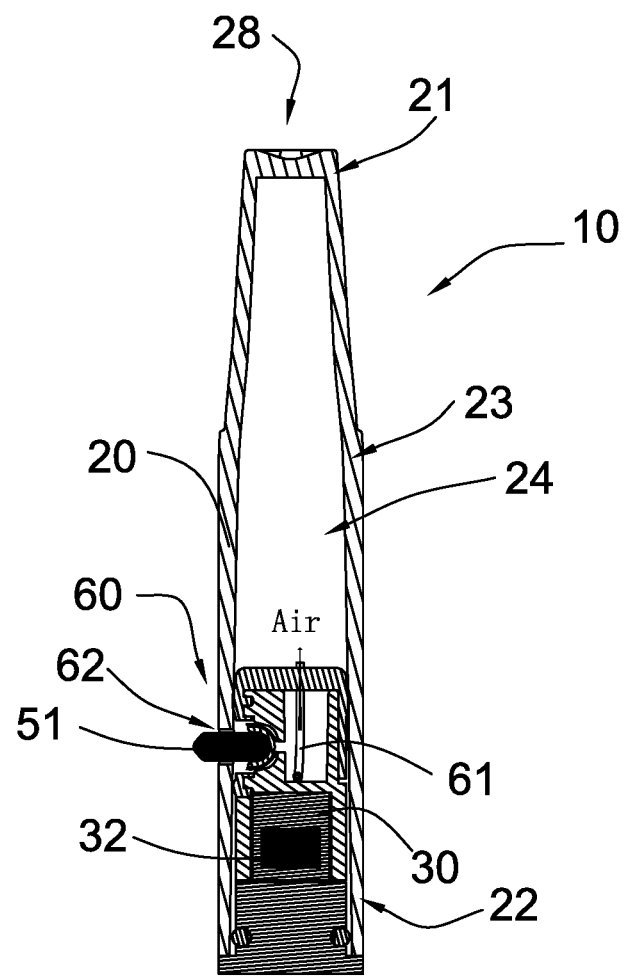
FIG. 4 is a sectional side view of the core cartridge along plane A-A of FIG. 2.
Figure 5:
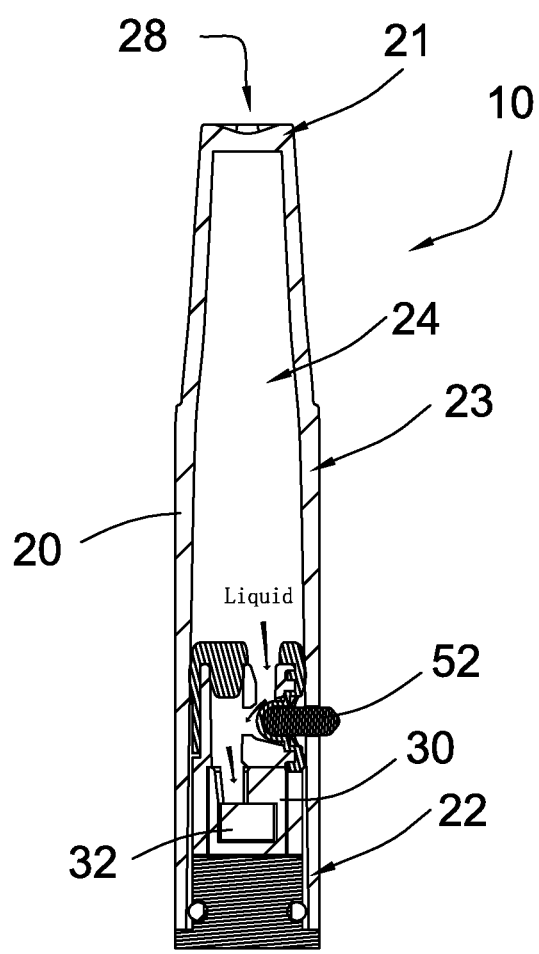
FIG. 5 is a sectional side view of the core cartridge along plane B-B of FIG. 2.

Referring to FIG. 4 of the drawings, the core cartridge 10 further comprises a pressure balancing arrangement 60 which comprises a pressure balancing tube 61 extended from the air switch 51 to the liquid storage compartment 24. The pressure balancing arrangement 60 further has at least one air gap 62 formed between the air switch 51 and the main housing 20 so that when the air switch 51 is actuated (such as being depressed), air may flow from ambient environment to the pressure balancing tube 61. In other words, the air gap 62 balances the pressure between the ambient environment and the liquid storage compartment 24. This enables supply of cigarette liquid from the liquid storage compartment 24 to the atomizer 30 to be more effective and smoother.

When the fuel switch 52 is actuated (such as being depressed), cigarette liquid is arranged to be guided to flow from the liquid storage compartment 24 to the atomizer 30 for producing cigarette vapor. Since the pressure in the liquid storage compartment 24 is adjusted to balance with the pressure in the ambient environment, cigarette liquid will be supplied to the atomizer 30 in a very smooth and effective manner.

The leakage prevention arrangement 40 further comprises a plurality of supporting members 44 provided at lower end portions of the vapor collection cavities 29 respectively, wherein each of the supporting members 44 has an extension portion 441 extended in the main housing 20 to define the corresponding drainage port 41 as a gap formed between the extension portion 441 and the inner surface 271 of the outer boundary wall 27 of the main housing 20.

Condensate or residuals formed on the inner surface 271 of the outer boundary wall 27 of the main housing 20 may be guided to reach the drainage ports 41 so that the condensate may pass through the drainage ports 41 and eventually flow back to the atomizer 30 for being re-vaporized.

Figure 9:
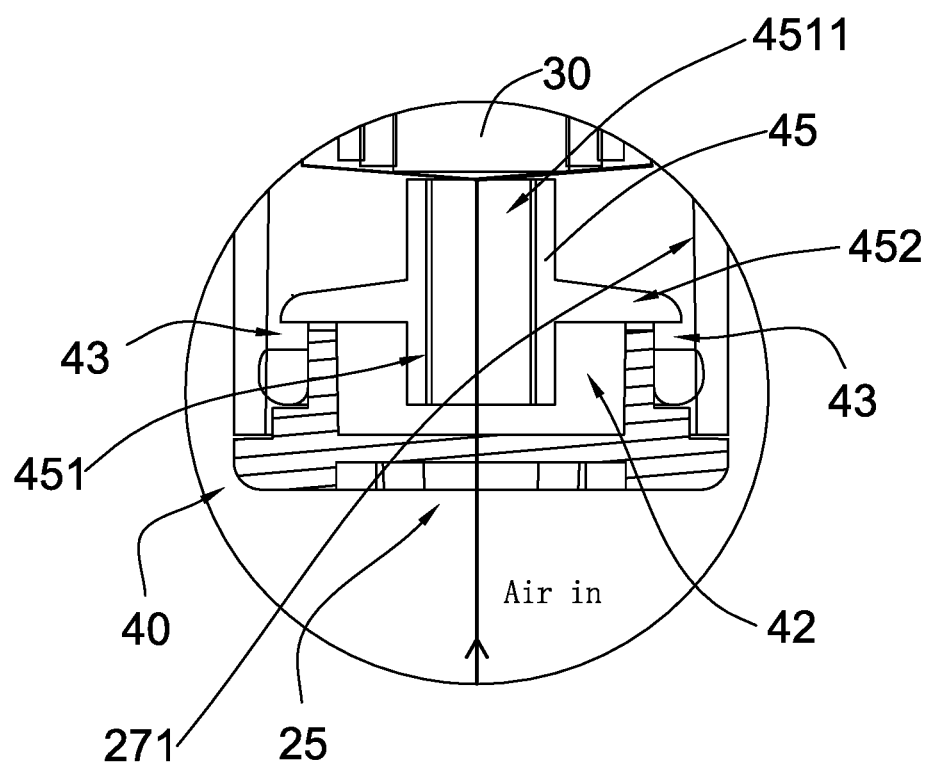
FIG. 9 is another schematic diagram of the core cartridge of the electronic cigarette according to the preferred embodiment of the present invention.
Figure 10:
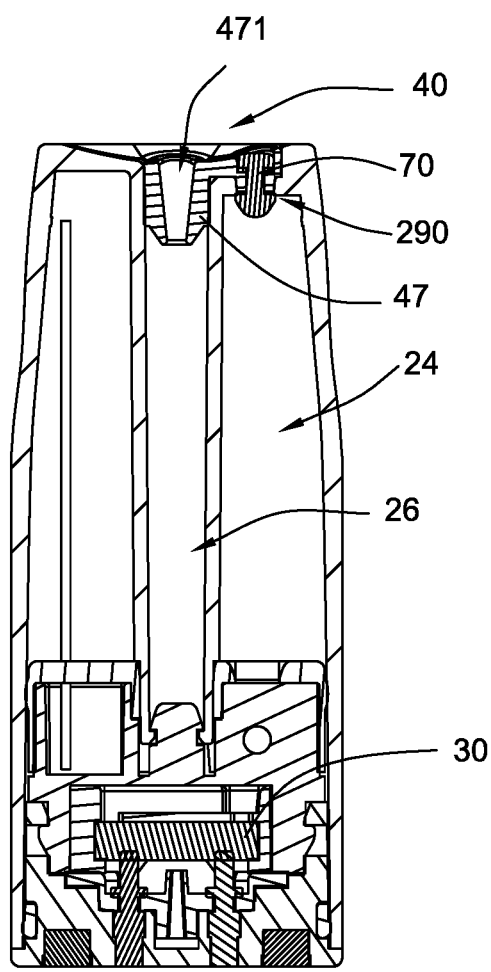
FIG. 10 is a sectional view of the core cartridge of the electronic cigarette according to the preferred embodiment of the present invention, illustrating the pressure balancing tube.

Referring to FIG. 6 and FIG. 9 of the drawings, the leakage prevention arrangement 40 further comprises a residual drainage port 43 and a residual storage cavity 42 formed in the main housing 20 at a position underneath the atomizer portion 22 for temporarily storing residual condensate which have not been guided and collected through the drainage ports 41. The residual drainage port 43 communicates the outer boundary wall 27 with the residual storage cavity 42.

Specifically, when the electronic cigarette stops working, a certain amount of condensate has been guided to pass through the drainage ports 41. Instead, the residual condensate can flow pass the drainage ports 41 and toward a bottom portion of the main housing 20. The residual condensate is then be guided to flow through the residual drainage port 43 and be eventually collected in the residual storage cavity 42. The residual storage cavity 42 communicates with the atomizer 30 so that the residual condensate stored in the residual storage cavity 42 can be guided to re-enter the atomizer 30 for being re-vaporized.

The leakage prevention arrangement 40 further comprises a base port member 45 supported in the main housing 20 to define the residual drainage port 43. The base port member 45 has a central portion 451 having a central channel 4511 and two extension flaps 452 extended from the central portion 451 to form the residual drainage ports 43 as the spaces between the extension flaps 452 and the inner surface 271 of the outer boundary wall 27 respectively.

Figure 8:
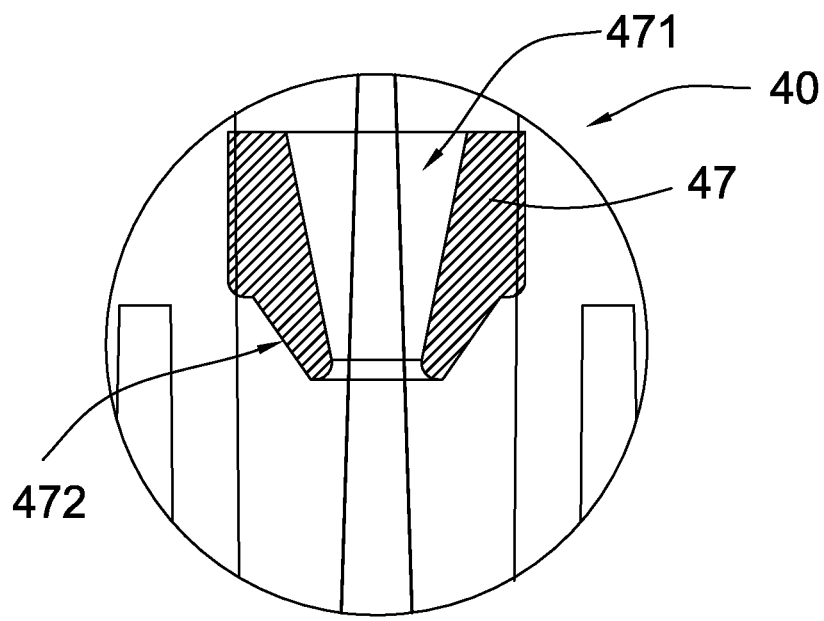
FIG. 8 is another schematic diagram of the core cartridge of the electronic cigarette according to the preferred embodiment of the present invention.

Moreover, referring to FIG. 8 of the drawings, the leakage prevention arrangement 40 further comprises a vapor control member 47 mounted in a top portion of the vapor releasing channel 26. The vapor control member 47 has a vapor passage 471 which communicate the vapor releasing channel 26 so that vapor from the atomizer 30 is arranged to pass through the vapor passage 471. As shown in FIG. 6 and FIG. 8 of the drawings, the vapor passage 471 has a tapered cross sectional shape when viewed from the front so that a diameter of the vapor passage 471 is gradually decreasing from the top toward the bottom thereof.

The vapor control member 47 has a slanted surface 472 facing downwardly toward the atomizer 30 in the vapor releasing passage 26. When the electronic cigarette stop working, a small amount of condensate or liquid residuals is formed on the slanted surface 472 or the inner sidewall 261 of the vapor releasing passage 26. These condensate or residuals are guided to flow back to the atomizer 30 along the vapor releasing passage 26 and provided at the bottom end portion thereof for being re-vaporized.

Thus, one may appreciate that the drainage ports 41 and the residual drainage ports 43 are designed to collect condensate formed on the inner surface 271 of the outer boundary wall 27 of the main housing 20 so as to form a double safeguards to collect and re-use the condensate left on the inner surface 271 of the outer boundary wall 27 and therefore prevent excessive culmination of condensate in any part of the main housing 20. The result is that the chance of condensate leak from the main housing 20 (especially when the electronic cigarette is not in use) can be minimized.

Moreover, the main housing 20 further has a fuel inlet 290 communicating with the liquid storage compartment 24 while the core cartridge 10 further comprises a fuel sealing cap 70 movably mounted on the main housing 20 for detachably covering the fuel inlet 290. In this preferred embodiment, the fuel sealing cap 70 is connected to the vapor control member 47 and may be pivotally moved with respect thereto.

The present invention, while illustrated and described in terms of a preferred embodiment and several alternatives, is not limited to the particular description contained in this specification. Additional alternative or equivalent components could be used to practice the present invention.

What is claimed is:

1. A core cartridge for electronic cigarette, comprising:
    a main housing having a mouth piece portion, an atomizer portion, a connecting portion extended between said mouth piece portion and said atomizer portion, a liquid storage compartment formed in said connecting portion and a an air inlet, said main housing further having an outer boundary wall and a vapor releasing channel extended from said atomizer portion to said connecting portion,
    an atomizer supported in said atomizer portion of said main housing, and
    a leakage prevention arrangement, which comprises at least one drainage port formed in said main housing, said drainage port communicating said outer boundary wall with said atomizer in such a manner that condensate formed on an inner surface of said outer boundary wall of said main housing is arranged to be guided to flow back to said atomizer through said drainage port,
    wherein said leakage preventing arrangement comprises two drainage ports formed in said atomizer portion of said main housing, each of said drainage ports communicating said outer boundary wall of said main housing with said atomizer, wherein when said electronic cigarette stops operating, condensate formed on an inner surface of said outer boundary wall is guided to flow through said drainage ports and eventually back to said atomizer,
    wherein said vapor releasing channel has a tapered cross-sectional shape when viewed from the front so that said inner sidewall of said vapor releasing channel is inclinedly extended from said mouth piece portion toward said atomizer portion, said main housing further has a vapor collection cavity formed between an outer sidewall of said vapor releasing channel and said corresponding inner surface of said outer boundary wall of said main housing,
    wherein said inner surface of said outer boundary wall is inclined so that a thickness of said vapor collection cavity gradually increased from said mouth piece portion toward said atomizer portion,
    wherein said leakage prevention arrangement further comprises a supporting member provided at a lower end portion of said vapor collection cavity, wherein said supporting member has an extension portion extended in said main housing to define said corresponding drainage port as a gap formed between said extension portion and said corresponding inner surface of said outer boundary wall of said main housing.

2. The core cartridge, as recited in claim 1, wherein said leakage prevention arrangement further comprise at least one residual drainage port and a residual storage cavity formed in said main housing at a position underneath said atomizer portion for temporarily storing residual condensate which is not collected through said drainage port, said residual drainage port communicating said outer boundary wall with said residual storage cavity.

3. The core cartridge, as recited in claim 2, wherein said leakage prevention arrangement further comprises a base port member supported in said main housing to define said residual drainage port, said base port member has a central portion having a central channel and at least one extension flap extended from said central portion to form said residual drainage port as a space between said extension flap and said corresponding inner surface of said outer boundary wall.

4. The core cartridge, as recited in claim 3, wherein said leakage prevention arrangement further comprises a vapor control member mounted in a top portion of said vapor releasing channel, said vapor control member having a vapor passage which communicates with said vapor releasing channel so that vapor from said atomizer is allowed to pass through said vapor passage.

5. The core cartridge, as recited in claim 4,
    wherein said vapor passage has a tapered cross sectional shape when viewed from the front so that a diameter of said vapor passage gradually decreases from a top toward a bottom thereof.

6. A core cartridge for electronic cigarette,
    a main housing having a mouth piece portion, an atomizer portion, a connecting portion extended between said mouth piece portion and said atomizer portion, a liquid storage compartment formed in said connecting portion and a an air inlet, said main housing further having an outer boundary wall and a vapor releasing channel extended from said atomizer portion to said connecting portion,
    an atomizer supported in said atomizer portion of said main housing,
    a leakage prevention arrangement, which comprises at least one drainage port formed in said main housing, said drainage port communicating said outer boundary wall with said atomizer in such a manner that condensate formed on an inner surface of said outer boundary wall of said main housing is arranged to be guided to flow back to said atomizer through said drainage port, and
    an air switch and a fuel switch provided on said main housing, and a pressure balancing arrangement which comprises a pressure balancing tube extended from the air switch to said liquid storage compartment, said pressure balancing arrangement further having at least one air gap formed between said air switch and said main housing so that when said air switch and said fuel switch are actuated, air from ambient environment is allowed to flow into said pressure balancing tube and balance a pressure between said ambient environment and that of said liquid storage compartment.

7. A core cartridge for electronic cigarette, comprising:

a main housing having a mouth piece portion, an atomizer portion, a connecting portion extended between said mouth piece portion and said atomizer portion, a liquid storage compartment formed in said connecting portion and a an air inlet, said main housing further having an outer boundary wall and a vapor releasing channel extended from said atomizer portion to said connecting portion:

an atomizer supported in said atomizer portion of said main housing;

a leakage prevention arrangement, which comprises at least one drainage port formed in said main housing, said drainage port communicating said outer boundary wall with said atomizer in such a manner that condensate formed on an inner surface of said outer boundary wall of said main housing is arranged to be guided to flow back to said atomizer through said drainage port.

an air switch and a fuel switch provided on said main housing; and a pressure balancing arrangement which comprises a pressure balancing tube extended from the air switch to said liquid storage compartment, said pressure balancing arrangement further having at least one air gap formed between said air switch and said main housing so that when said air switch and said fuel switch are actuated, air from ambient environment is allowed to flow into said pressure balancing tube and balance a pressure between said ambient environment and that of said liquid storage compartment, wherein said leakage prevention arrangement further comprises at least one residual drainage port and a residual storage cavity formed in said main housing at a position underneath said atomizer portion for temporarily storing residual condensate which is not collected through said drainage port, said residual drainage port communicating said outer boundary wall with said residual storage cavity, wherein said leakage prevention arrangement further comprises a vapor control member mounted in a top portion of said vapor releasing channel, said vapor control member having a vapor passage which communicates with said vapor releasing channel so that vapor from said atomizer is allowed to pass through said vapor passage.

wherein said vapor passage has a tapered cross sectional shape when viewed from the front so that a diameter of said vapor passage gradually decreases from a top toward a bottom thereof.

8. The core cartridge, as recited in claim 1, wherein said main housing further has a vapor outlet formed on said mouth piece portion for allowing vapor to be discharged therethrough, said vapor outlet communicating with said vapor releasing channel so that vapor passing through said vapor releasing channel is allowed to be discharged out of said main housing through said vapor outlet.

9. The core cartridge, as recited in claim 6, wherein said main housing further has a vapor outlet formed on said mouth piece portion for allowing vapor to be discharged therethrough, said vapor outlet communicating with said vapor releasing channel so that vapor passing through said vapor releasing channel is allowed to be discharged out of said main housing through said vapor outlet.

10. The core cartridge, as recited in claim 7, wherein said main housing further has a vapor outlet formed on said mouth piece portion for allowing vapor to be discharged therethrough, said vapor outlet communicating with said vapor releasing channel so that vapor passing through said vapor releasing channel is allowed to be discharged out of said main housing through said vapor outlet.

11. The core cartridge, as recited in claim 1, wherein said atomizer comprises a heating element which is communicated with said liquid storage compartment and is arranged to vaporize said e-cigarette liquid controllably released from said atomizer.

12. The core cartridge, as recited in claim 7, wherein said atomizer comprises a heating element which is communicated with said liquid storage compartment and is arranged to vaporize said e-cigarette liquid controllably released from said atomizer.

* * * * *